(12) United States Patent  
Biedermann (10) Patent No.: US 11,166,753 B2  
(45) Date of Patent: Nov. 9, 2021

(54) ANCHORING ASSEMBLY FOR ANCHORING A ROD TO A BONE OR A VERTEBRA

(71) Applicant: BIEDERMANN TECHNOLOGIES GMBH & CO. KG, Donaueschingen (DE)

(72) Inventor: Timo Biedermann, Trossingen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

(21) Appl. No.: 16/789,044

(22) Filed: Feb. 12, 2020

(65) Prior Publication Data

US 2020/0253644 A1   Aug. 13, 2020

Related U.S. Application Data

(60) Provisional application No. 62/804,920, filed on Feb. 13, 2019.

(30) Foreign Application Priority Data

Feb. 13, 2019   (EP) ..................................... 19157004

(51) Int. Cl.  
A61B 17/70   (2006.01)

(52) U.S. Cl.  
CPC ...... A61B 17/7032 (2013.01); A61B 17/7037 (2013.01)

(58) Field of Classification Search  
CPC ............ A61B 17/7032; A61B 17/7035; A61B 17/7037

(Continued)

(56) References Cited

U.S. PATENT DOCUMENTS 5,873,878 A * 2/1999 Harms ............... A61B 17/7032  
606/308  
7,955,359 B2   6/2011 Matthis et al.  
(Continued)

FOREIGN PATENT DOCUMENTS

EP   1 743 584 A1   1/2007  
EP   1 935 358 A1   6/2008  
(Continued)

OTHER PUBLICATIONS

Extended European Search Report for Application No. 19157004.3, dated Sep. 3, 2019, 9 pages.

*Primary Examiner* — Eduardo C Robert  
*Assistant Examiner* — David C Comstock  
(74) *Attorney, Agent, or Firm* — Lewis Roca Rothgerber Christie LLP (57) ABSTRACT

An anchoring assembly for anchoring a rod to a bone or vertebra includes a shank and a receiving part pivotably connected to one another, the receiving part defining a channel for the rod, a pressure element for locking the shank with the receiving part, first and second rods with different diameters configured to be interchangeably received in the channel, and first and second closure elements configured to interchangeably cooperate with the receiving part. The first closure element acts on the selected rod in the receiving part such that the rod exerts pressure on the pressure element to simultaneously lock the shank with the receiving part and fix the rod in the channel. The second closure element cooperates with the receiving part to act on the pressure element to lock the shank with the receiving part, and to act separately on the selected rod to fix the rod in the channel.

23 Claims, 7 Drawing Sheets

(58) Field of Classification Search
USPC ....... 606/264, 266, 267, 268, 270, 272, 279, 606/305, 306
See application file for complete search history.

(56) References Cited

U.S. PATENT DOCUMENTS

| | | | |
|---|---|---|---|
| 8,257,399 B2 | 9/2012 | Biedermann et al. | |
| 9,339,302 B2 | 5/2016 | Biedermann et al. | |
| 2007/0055241 A1* | 3/2007 | Matthis | A61B 17/7037 606/267 |
| 2007/0118123 A1* | 5/2007 | Strausbaugh | A61B 17/7049 606/272 |
| 2008/0086132 A1* | 4/2008 | Biedermann | A61B 17/7032 606/279 |
| 2008/0215100 A1* | 9/2008 | Matthis | A61B 17/7032 606/309 |
| 2009/0012567 A1* | 1/2009 | Biedermann | A61B 17/7032 606/264 |
| 2009/0318969 A1* | 12/2009 | Matthis | A61B 17/7031 606/254 |
| 2010/0286731 A1* | 11/2010 | Biedermann | A61B 17/7037 606/264 |
| 2012/0041490 A1* | 2/2012 | Jacob | A61B 17/7032 606/264 |
| 2013/0110172 A1* | 5/2013 | Biedermann | A61B 17/7035 606/278 |
| 2014/0142633 A1* | 5/2014 | Jackson | A61B 17/683 606/273 |

FOREIGN PATENT DOCUMENTS

| | | |
|---|---|---|
| EP | 2 070 485 A1 | 6/2009 |
| EP | 2 468 197 A1 | 6/2012 |
| EP | 2 559 391 A1 | 2/2013 |
| EP | 2 668 919 A1 | 12/2013 |

* cited by examiner

ANCHORING ASSEMBLY FOR ANCHORING A ROD TO A BONE OR A VERTEBRA

CROSS-REFERENCE TO RELATED APPLICATION(S)

The present application claims priority to and the benefit of U.S. Provisional Patent Application No. 62/804,920, filed Feb. 13, 2019, the contents of which are hereby incorporated by reference in their entirety, and claims priority from European Patent Application EP 19 157 004.3, filed Feb. 13, 2019, the contents of which are hereby incorporated by reference in their entirety.

BACKGROUND

Field

The application relates to an anchoring assembly for anchoring a rod to a bone or a vertebra, wherein the anchoring assembly includes at least two rods having different diameters.

Description of Related Art

A bone anchoring assembly of this type is known from U.S. Pat. No. 8,257,399 B2. The bone anchoring assembly includes a bone anchoring device including a shaft and a head pivotably connected to said shaft and having two substantially vertically extending legs defining a channel, a pressure element, and a two-part fixation element that includes a first outer screw with a coaxial threaded bore in which a second inner screw is inserted. The outer screw can fix the pivotal position of the head by pressing the pressure element onto the head. The inner screw acts onto the rod. Thereby the rod can be fixed independently of the head. The assembly further includes two rods having different diameters.

U.S. Pat. No. 7,955,359 B2 describes a polyaxial bone anchoring device that includes an anchoring element having a head, a receiving portion for receiving the head and a recess for receiving a rod, and a pressure element configured to couple to the head. A first closure element for simultaneously fixing the rod in the recess and the head in the receiving portion can be used interchangeably with a second closure element that is configured to fix the head and the rod independently.

A further type of closure mechanism for a polyaxial bone anchoring device is described in U.S. Pat. No. 9,339,302 B2. The polyaxial bone anchoring device described in this document includes a bone anchoring element with a shank and a head that is pivotably received in a receiving part. The receiving part also has a channel for receiving a rod. A pressure element is configured to be arranged in the receiving part and to exert pressure onto and lock the head. Further, a locking assembly is provided that is insertable into the channel, where locking assembly includes a first locking member having a bore and a second locking member provided in the bore. The polyaxial bone anchoring device allows locking of the head of the bone anchoring element in the receiving part and the rod in a sequential manner using a tool with only a single drive portion. By this sequential locking mechanism, it is possible to first lock or at least preliminarily clamp the head, and thereafter finally lock the rod and the head.

SUMMARY

While the bone anchoring devices and assemblies of the prior art described above enable a wide range of applications, there is a demand for providing bone anchoring devices, assemblies, or parts thereof that have greater versatility, with the smallest possible number of basic components.

It is, therefore, an object of the invention to provide a bone anchoring assembly and a closure element for a polyaxial bone anchoring device that is versatile in its application and at the same time simple in its structure.

According to an aspect, the anchoring assembly for anchoring a rod to a bone or a vertebra includes a bone anchoring device including a shank and a receiving part pivotably connectable to the shank, the receiving part having a channel for receiving a rod, a pressure element configured to lock an angular position of the shank relative to the receiving part, at least a first rod and a second rod having different diameters and configured to be interchangeably received in the channel, a first closure element cooperating with the receiving part, the first closure element configured to act upon the first rod or the second rod such that the first rod or the second rod exert pressure onto the pressure element to lock an angular position of the receiving part relative to the shank and to fix the first rod or the second rod in the channel simultaneously, and a second closure element cooperating with the receiving part, the second closure element configured to act on the pressure element and on the first rod or the second rod to lock and angular position of the receiving part relative to the shank and to fix the first rod or the second rod separately from one another, wherein the first closure element and the second closure element are interchangeable.

The anchoring assembly permits selection between rods of different diameters when using the bone anchoring device, and simultaneously selection between different locking mechanisms. A first locking mechanism includes the first closure element that is configured to lock and angular position of the receiving part relative to the shank on the one hand and to fix the position of the rod in the channel of the receiving part on the other hand in one single step. In the same manner, releasing of the locking of the angular position and loosening of the fixation of the rod is effected simultaneously when loosening the first closure element.

When using the second closure element instead of the first closure element, a second locking mechanism can be implemented. With the second locking mechanism, the locking of the angular position of the receiving part relative to the shank on the one hand and the fixation of the position of the rod in the channel of the receiving part on the other hand can be effected separately.

In a first embodiment, the second closure element is adapted to lock the angular position of the receiving part relative to the shank and to fix the position of the rod independently from each other. In a second embodiment, the second closure element is adapted to lock the angular position of the receiving part relative to the shank and to fix the position of the rod in the channel sequentially. Releasing of the locking of the angular position of the receiving part relative to the shank and loosening the fixation of the rod can be effected independently or sequentially, according to these first and second embodiments, respectively.

Hence, the first closure element, the second closure element of the first embodiment, and the second closure element of the second embodiment are fully interchangeable within one polyaxial bone anchoring device, and can each be used with rods of different diameter. The different diameters may be, for example, 5.5 mm or 6.0 mm, which are typical rod diameters used in stabilization of the spine.

Each of the closure elements permit use of rods having different diameters.

In this way, the inventory is limited or reduced to a few basic components. Simultaneously, the number of applications, specifically the variety of surgical steps to be carried out with the anchoring assembly, is increased.

According to another aspect, a closure element for a polyaxial bone anchoring device includes a first locking member having a first end and a second end, a bore passing through the first locking member from the first end to the second end, the bore having an internal thread with a lower thread flank that is closest to the second end, and a second locking member having an external thread, wherein the second locking member is provided in the threaded bore of the first locking member, the second locking member having a first end directed towards the first end of the first locking member, a second end, and an abutment surface close to the second end, the abutment surface facing towards the first end of the second locking member, wherein a stop is provided to limit an advancement of the second locking member relative to the first locking member towards the first end of the first locking member, and wherein the stop is effected by the abutment of the abutment surface of the second locking member against the lower thread flank of the first locking member.

The second closure element according to this aspect is a two part closure element that may be designed in a first embodiment for independent locking of the angular position of the receiving part relative to the shank and fixation of the rod. Similarly, the second closure element according to this aspect is a two part closure element that may be used in a second embodiment for locking of the receiving part relative to the shank and for fixation of the rod in a sequential manner. For both of these locking mechanisms, the second locking member may be identical and combined with a suitable first locking member, respectively, to form an appropriate or desired second closure element. Thereby the number of components in a kit can be further reduced.

Lastly, a further aspect of an anchoring assembly includes a bone anchoring device including a shank and a receiving part pivotably connectable to the shank, the receiving part having a channel for receiving a rod, a pressure element configured to lock an angular position of the shank relative to the receiving part, at least a first rod and a second rod having different diameters and configured to be interchangeably received in the channel, and a second closure element of the first embodiment and a second closure element of the second embodiment as described above which are interchangeable.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
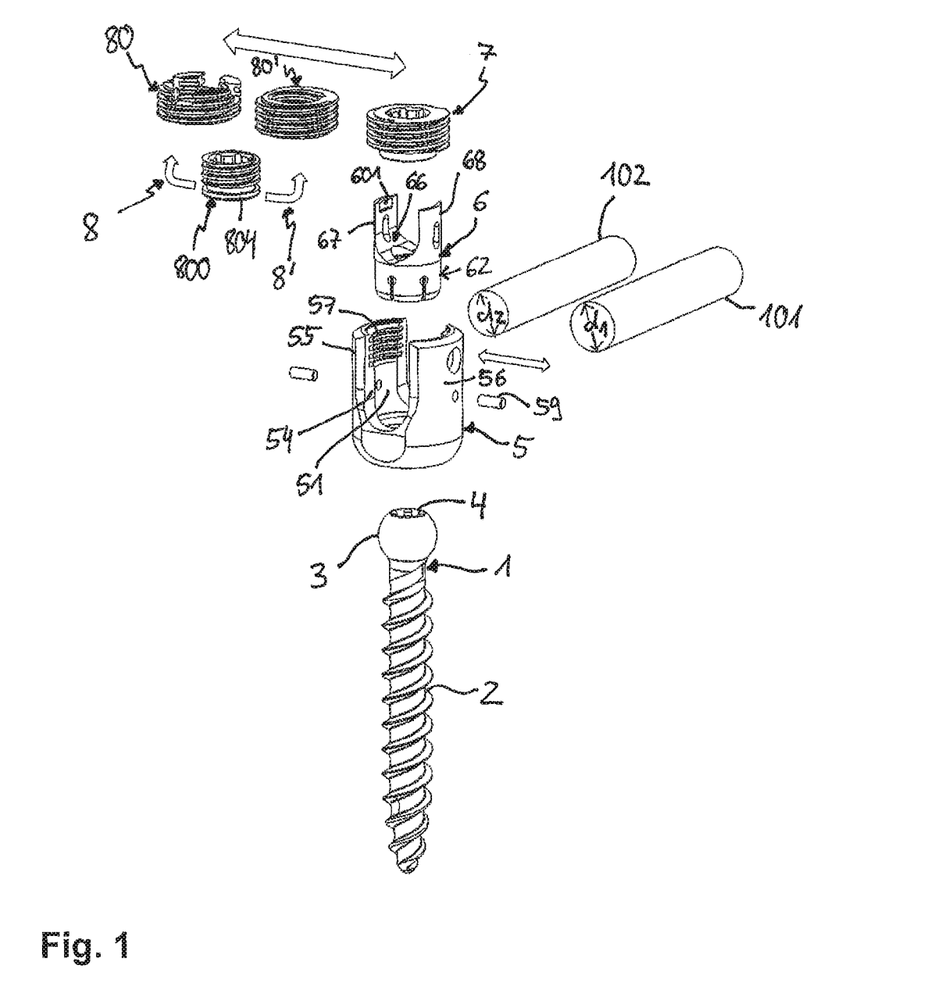
FIG. 1 shows a perspective exploded view of an embodiment of the bone anchoring assembly.
Figure 2:
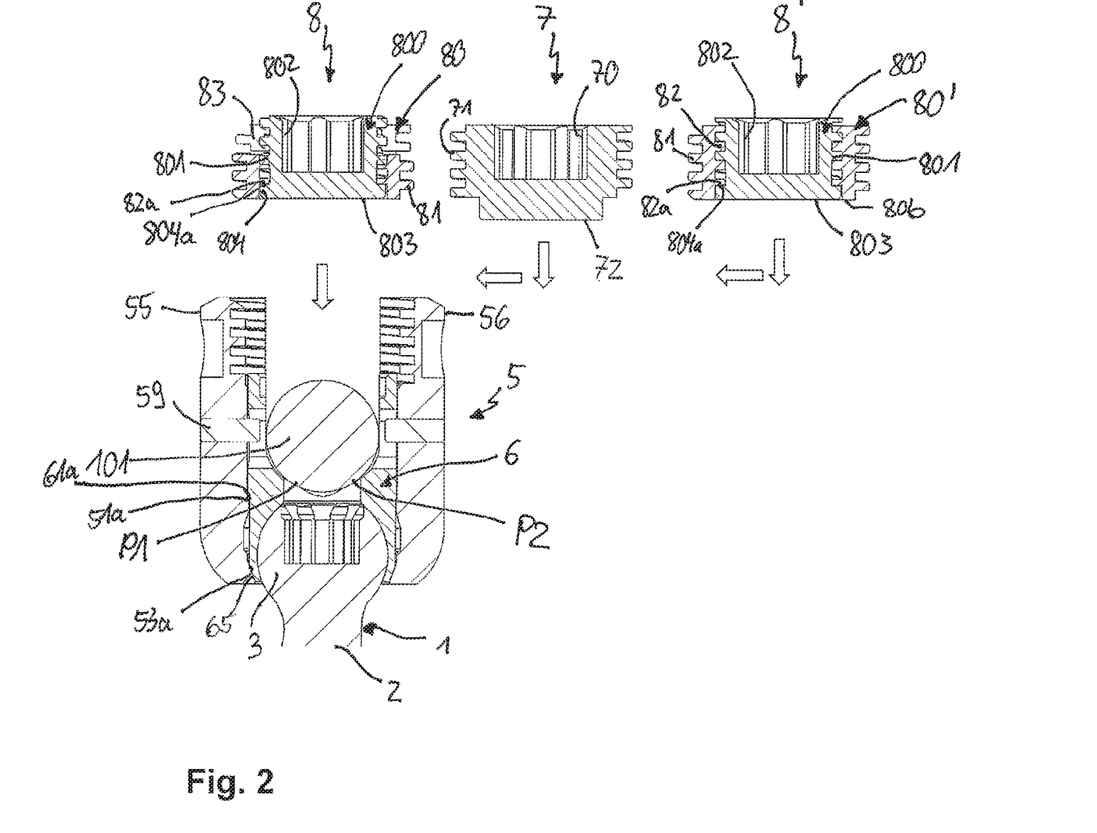
FIG. 2 shows a cross-sectional view of the embodiment of the anchoring assembly of FIG. 1 with various different closure elements, wherein the cross-section is taken in a plane extending through a center of the receiving part and perpendicular to a longitudinal axis of an inserted rod.
Figure 3:
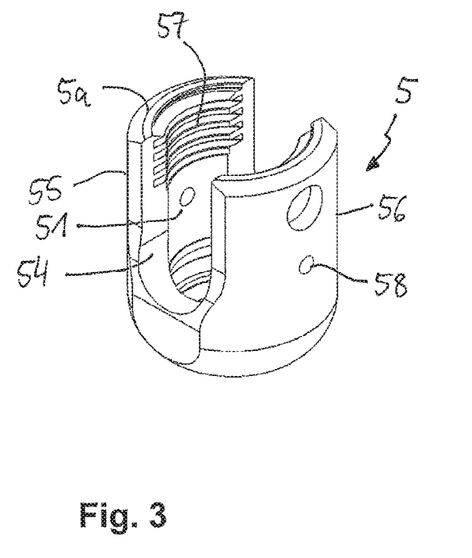
FIG. 3 shows a perspective view from a top of a receiving part of the bone anchoring assembly of FIGS. 1 and 2.
Figure 4:
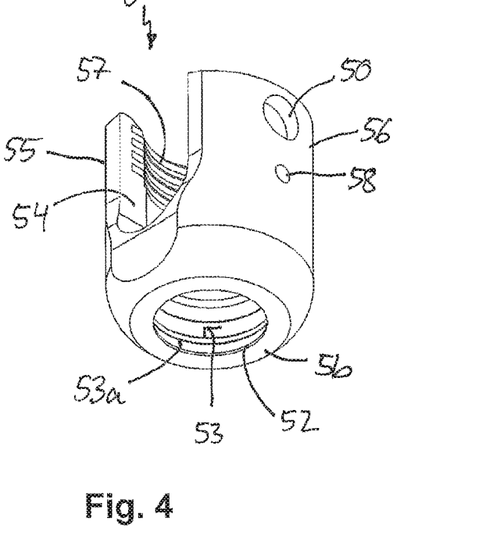
FIG. 4 shows a perspective view from a bottom of the receiving part of FIG. 3.
Figure 5:
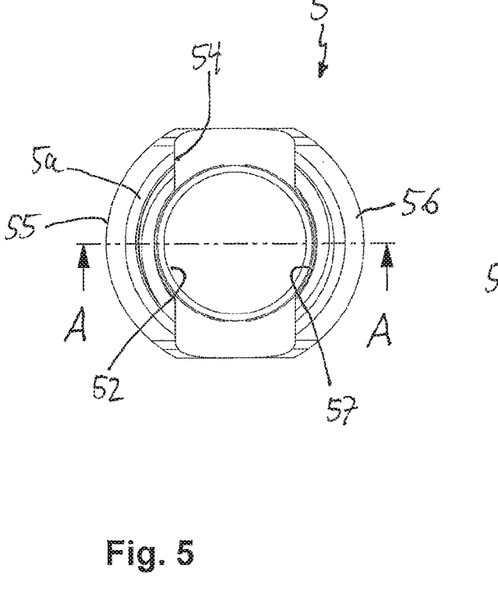
FIG. 5 shows a top view of the receiving part of FIGS. 3 and 4.
Figure 6:
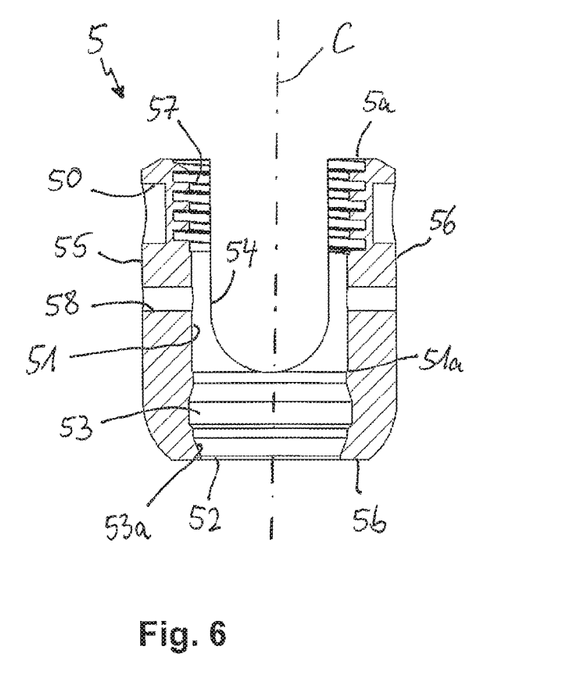
FIG. 6 shows a cross-sectional view of the receiving part of FIGS. 3 to 5, the cross-section taken along line A-A in FIG. 5.
Figure 7:
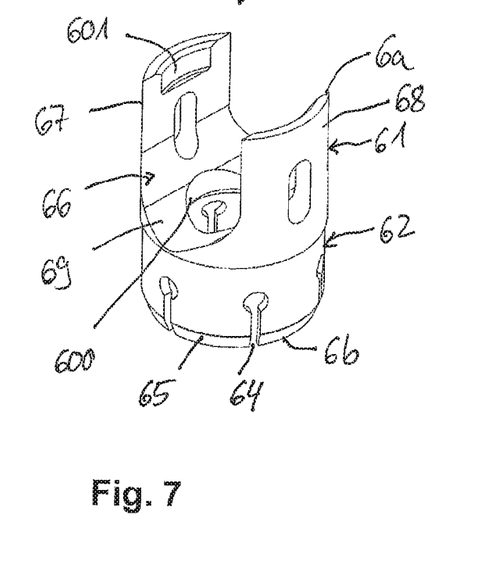
FIG. 7 shows a perspective view from a top of a pressure element of the bone anchoring assembly of FIGS. 1 and 2.
Figure 8:
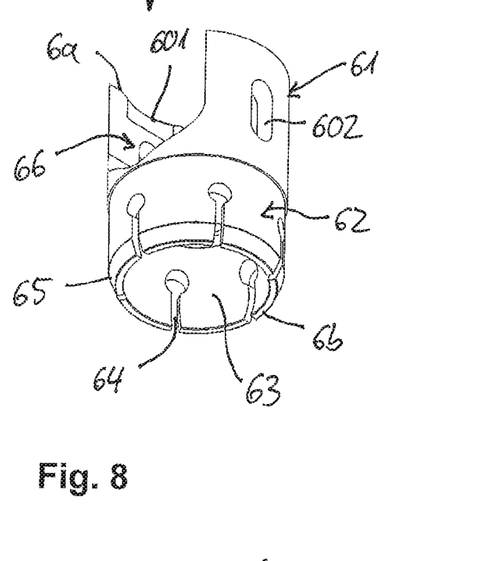
FIG. 8 shows a perspective view from a bottom of the pressure element of FIG. 7.
Figure 9:
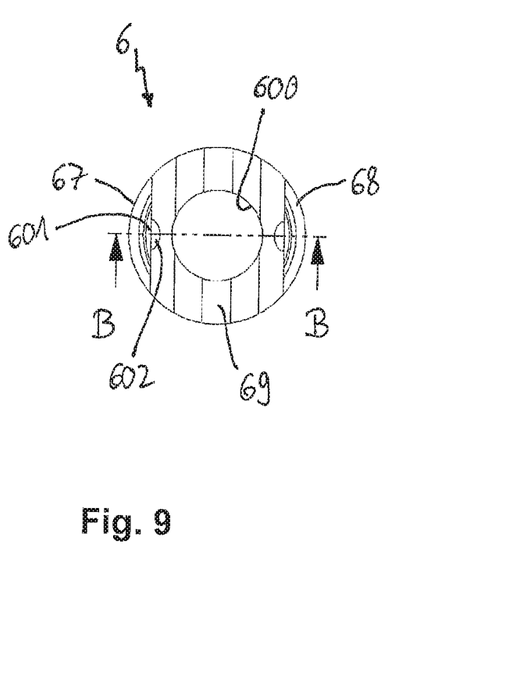
FIG. 9 shows a top view of the pressure element of FIGS. 7 and 8.
Figure 10:
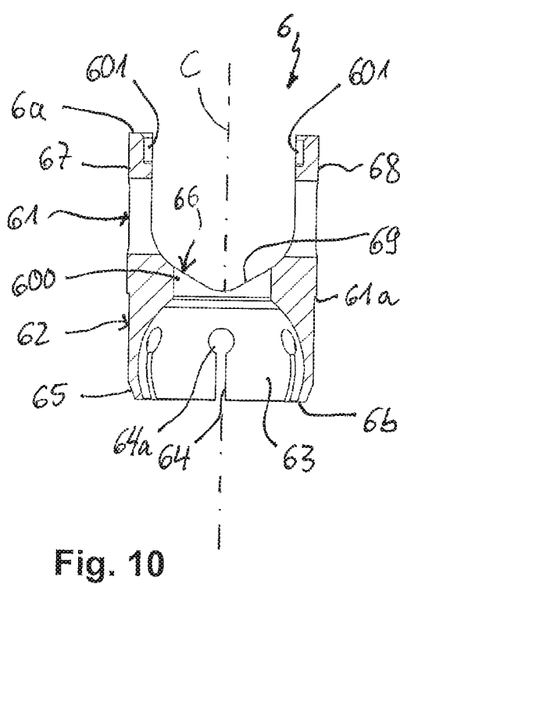
FIG. 10 shows a cross-sectional view of the pressure element of FIGS. 7 to 9, the cross-section taken along line B-B in FIG. 9.

An anchoring assembly according to an embodiment is shown in FIGS. 1 and 2. The anchoring assembly includes a polyaxial bone anchoring device and at least a first rod 101 having a first diameter $d_1$ and a second rod 102 having a second diameter $d_2$, wherein the second diameter $d_2$ is smaller than the first diameter $d_1$. The bone anchoring device includes a bone anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to one of the first rod 101 or the second rod 102, respectively. In the receiving part 5, a pressure element 6 is arranged to exert pressure onto the head 3 of the bone anchoring element 1.

Additionally, the anchoring assembly includes a first closure element 7 that is configured to simultaneously lock an angular position of the bone anchoring element 1 relative to the receiving part 5 and to fix the position of one of the first rod 101 or the second rod 102 within the receiving part 5. A second closure element 8 may be assembled with the receiving part 5 in an interchangeable manner with the first closure element 7. The second closure element 8 is configured to separately lock the angular position of the receiving part 5 relative to the shank 2 and to fix the first rod 101 or the second rod 102 in the receiving part 5.

A first embodiment of the second closure element 8 includes a first or outer locking member 80 and a second or inner locking member 800 configured to cooperate with the first locking member 80. The first locking member 80 and the second locking member 800 are configured to lock the receiving part 5 relative to the shank 2 and the first rod 101 or the second rod 102 in the receiving part in an independent manner. A second embodiment of the second closure element 8' includes a first or outer locking member 80' that cooperates with the second or inner locking member 800, where the second or inner locking member 800 may be identical to the second locking member of the first embodiment. The first locking member 80' and the second locking member 800 are configured to sequentially lock the angular position of the receiving part 5 relative to the shank 2 and to fix the first rod 101 or the second rod 102. The first and the second embodiments of the second closure element 8, 8' can be used interchangeably.

The first rod 101 and the second rod 102 may each have a circular cross-section along its entire length. Alternatively, they may have a circular cross-section only in certain sections, for example in sections of the rod that are configured to be received in the receiving part 5. The first rod 101 and the second rod 102 may have such a size that they are rotatable around the rod axis and/or displaceable in a channel 54 of the receiving part 5. Preferably, the rods have a smooth outer surface. The first rod 101 and the second rod 102 may have different shapes.

Referring to FIGS. 3 to 6, the receiving part 5 has a first or top end 5a and a second or bottom end 5b opposite to the top end 5a. The receiving part 5 may have a substantially cylindrical outer shape with a longitudinal axis C extending through the top end 5a and the bottom end 5b. Coaxially with the longitudinal axis C, a passage 51 is provided extending from the top end 5a to the bottom end 5b, and forming an opening 52 at the bottom end 5b. At a distance from the top end 5a the passage widens into an accommodation space 53 that is configured to receive the head 3 and at least a portion of the pressure element 6. Adjacent to the opening 52 at the bottom end 5b, the accommodation space 53 narrows towards the opening 52, for example, with a tapered surface, in particular with a conical surface that may cooperate with a portion of the pressure element 6 to clamp by friction or completely lock the head 3 in the receiving part 5. The width of the opening 52 may be greater than a greatest width of the head 3 so that the head 3 may be inserted from the bottom end 5b into the accommodation space 53. Hence, the embodiment shows a bottom loading polyaxial bone anchoring device. To enable the bottom loading, the width of the accommodation space 53 is such that the pressure element 6 can expand therein to permit the insertion of the head 3, as explained below.

The receiving part 5 further has a substantially U-shaped recess 54 starting at the top end 5a and extending in the direction of the bottom end 5b. By means of the U-shaped recess 54, two free legs 55, 56 are formed that define a channel open towards the first end 5a for receiving the first rod 101 or the second rod 102. Adjacent to the top end 5a, a portion with an internal thread 57 is provided at the inner surface of the legs 55, 56. In the embodiment shown, the internal thread 57 is a flat thread having substantially horizontal upper and lower thread flanks. This thread form reduces splaying of the legs 55, 56 when the first closure element 7 or the second closure element 8, 8' is tightened therebetween. However, other thread forms may be implemented for the internal thread 57 as well. Moreover, a pair of transverse holes 58 may extend through the legs 55, 56, respectively in a direction perpendicular to the central axis C and at a position approximately at the center of each leg 55, 56 in the circumferential direction. The transverse holes 58 may serve for accommodating pins 59 that extend through the holes into the channel. The pins 59 are configured to engage the pressure element 6 to form a securing device to secure the pressure element 6 against rotation. In addition, the pins may limit an upward movement of the pressure element 6. At an upper portion of the legs, substantially at the center in a circumferential direction, recesses 50 may be formed for engagement with a tool. In the inner wall forming the passage 51, an edge 51a may be provided for limiting downward movement of the pressure element 6.

In some embodiments, the pressure element 6 may be formed as a monolithic part, with a first or upper end 6a and a second or lower end 6b opposite to the upper end 6a. Adjacent to the upper end 6a, the pressure element has a substantially cylindrical first portion 61 with an outer diameter that is only slightly smaller than an inner diameter of the passage 51 so that the first portion 61 can be received in the passage 51 and move therein in an axial direction. Adjacent to the lower end 6b, a second substantially cylindrical portion 62 is formed that is configured to extend at least partially into the accommodation space 53 of the receiving part 5. The second portion 62 may have a slightly smaller outer width compared to the first portion 61, so that a step 61a is formed between the first portion 61 and the second portion 62. With the step 61a, the pressure element 6 may rest on the edge 51a formed in the inner wall of the passage 51 of the receiving part 5. Adjacent to the lower end 6b, a substantially spherical segment-shaped recess 63 is formed in the second portion 62 which is designed and sized so as to frictionally hold the head 3 of the bone anchoring element 1 therein. A plurality of longitudinal slits 64 are open to the lower end 6b and extend into a wall of the second portion 62 up to a distance from the lower end 6b. The longitudinal slits 64 render the second portion 62 flexible. The number and shape of the slits 64 may be selected such that a desired flexibility is achieved. To enhance the flexibility, the slits may be widened at their closed ends 64a. Adjacent to the lower end 6b, the outer surface of the second portion 62 has a tapered portion 65, preferably a conically-tapered portion, that is configured to cooperate with the narrowing portion 53a of the accommodation space 53 of the receiving part 5. By means of the cooperating surfaces 65, 53a of the pressure element 6 and of the receiving part 5, respectively, the flexible second portion 62 of the pressure element 6 can be compressed to clamp or lock the head 3 therein. As further shown in FIG. 2, the second portion 62 of the pressure element 6 is shaped and sized such that when the step 61a abuts against the edge 51a, the tapered surfaces 65 of the pressure element 6 and 53a of the receiving part 5 are in contact and the pressure element 6 is at a lower position.

Adjacent to the upper end 6a, a recess 66 forms two open legs 67, 68 that preferably have opposite flat inner walls, and a base 69. The base 69 has a substantially V-shaped contour when viewed in a plane including the central axis C. The V-shaped contour of the base 69 may be rounded at its deepest position and at the transitions to the flat sidewalls. The distance between the inner sidewalls of the recess 66 and an angle of the V-shape of the base 69 is such that at least the first rod 101 having the first diameter $d_1$ and the second rod 102 having the second diameter $d_2$ can be received in the recess 66. More generally, the recess 66 is shaped and sized such that a rod with a largest diameter and a rod with a smallest diameter can be inserted and contact the base 69 at two contact lines P1, P2 that are parallel to the rod axis, respectively as shown, for example, in FIG. 2. The depth of the recess 66 is such that for all rods having a diameter between the smallest and the largest diameter, the legs 67, 68 extend above the upper surface of the inserted rod.

Moreover, the pressure element 6 includes a coaxial bore 600 that allows for accessing of the recess 4 of the head 3 with a tool. In addition, two opposite recesses 601 are formed in the inner wall of the legs 67, 68 and extend from the upper end 6a toward the base 69. The recesses 601 may have a cylinder segment shape. In particular, the recesses 601 have a depth in the axial direction such that a gap is provided between the pressure element 6 and the first closure element 7 or the second locking member 800 of the second closure element 8, 8' in the axial direction, i.e., in a direction parallel to the central axis C, when any of the first rod 101 or the second rod 102 is inserted and contacted by the first closure element 7 or the second locking member 800. Thereby an interaction of the pressure element 6 with the first closure element 7 or with the second locking member 800 of the second closure element 8, 8' is inhibited or reduced. At approximately the center of the legs 67, 68 in a circumferential direction, each of the legs has an elongate hole 602, the longer axis of which extends substantially parallel to the central axis C. The elongate holes 602 are configured to be engaged by the pins 59. The cooperation between the pins 59 and the elongate holes 602 prevents rotation of the pressure element 6 in the receiving part. Furthermore, the pins 59 form a stop against an upward movement of the pressure element 6 when the head 3 is inserted through the lower opening 52 of the receiving part into the recess 63 of the pressure element 6.

Figure 11:
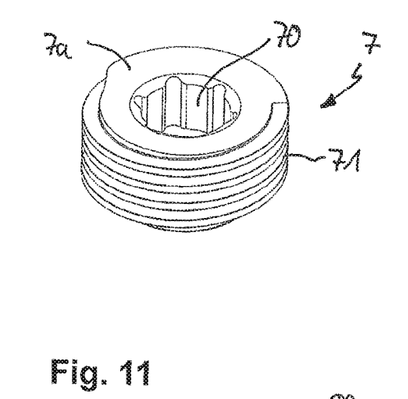
FIG. 11 shows a perspective view from a top of a first closure element of the bone anchoring assembly of FIGS. 1 and 2.
Figure 12:
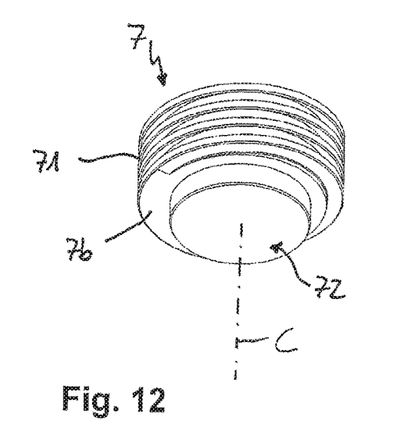
FIG. 12 shows a perspective view from a bottom of the first closure element of FIG. 11.
Figure 22:
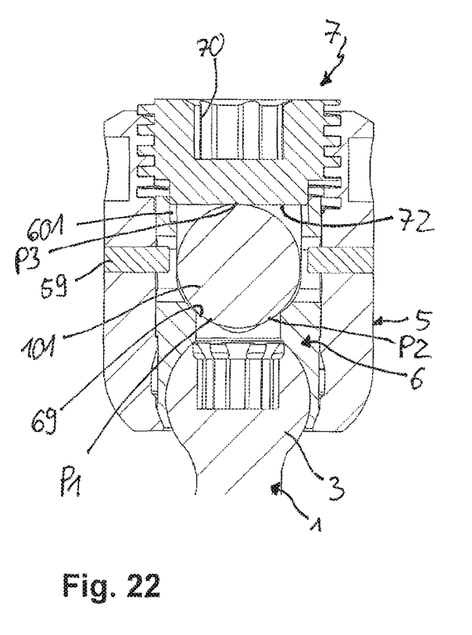
FIG. 22 shows a cross-sectional view of the anchoring assembly of FIGS. 1 and 2, with a rod having a first diameter and using the first closure element.
Figure 23:
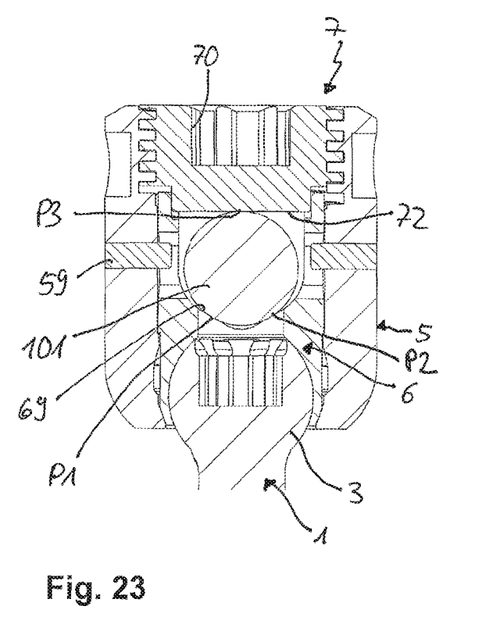
FIG. 23 shows a cross-sectional view of the anchoring assembly of FIGS. 1 and 2, with a rod having a second diameter smaller than the first diameter and using the first closure element.

Referring to FIGS. 1 to 2 and further to FIGS. 11 and 12, the first closure element 7 will be described. The first closure element 7 in this embodiment is a single part closure element in the form of an inner screw or set screw. The first closure element 7 has an upper end 7a and a lower end 7b and an external thread 71 that cooperates with the internal thread 57 provided at the legs 55, 56 of the receiving part 5. At the upper end 7a, a recess 70 for engagement with a screwing-in tool is formed. At the lower end, a cylindrical projection 72 is provided, an outer diameter of which is slightly smaller than the inner diameter of the recess 66 of the pressure element 6 at the position of the recesses 601. As a result, when the pressure element 6 is in the receiving part 5 and the first closure element 7 is screwed in between the legs 56, 57, the projection 72 does not directly exert a force onto the pressure element 6 in an axial direction, as depicted in FIGS. 22 and 23. The axial length of the projection 72 is such that when the pressure element 6 is in the receiving part and the head 3 has been inserted, the projection 72 is configured to contact any rod between a smallest diameter and a largest diameter that is receivable in the recess 66 without exerting direct pressure onto the pressure element 6.

Figure 13:
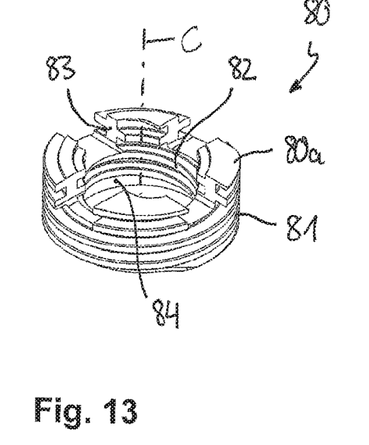
FIG. 13 shows a perspective view from a top of a first embodiment of a first locking member of a second closure element of the bone anchoring assembly shown in FIGS. 1 and 2.
Figure 14:
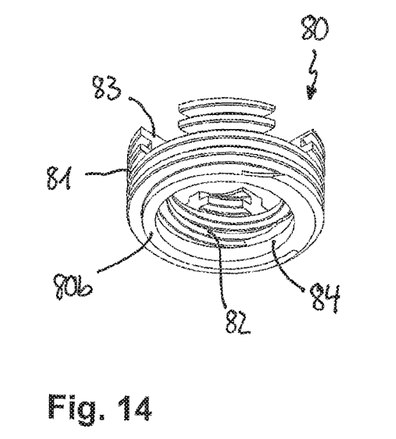
FIG. 14 shows a perspective view from a bottom of the first locking member shown in FIG. 13.
Figure 20:
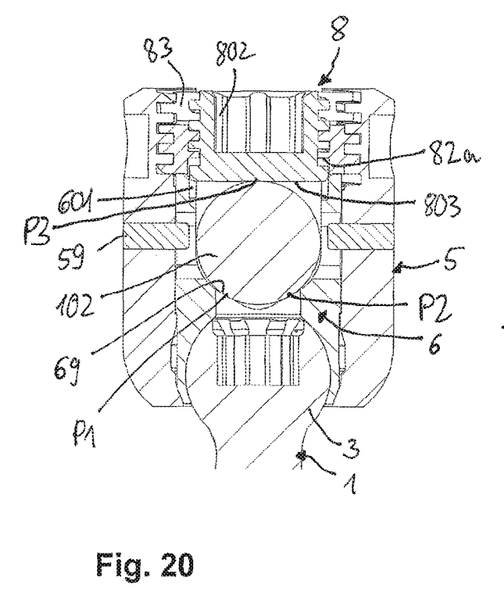
FIG. 20 shows a cross-sectional view of the anchoring assembly of FIGS. 1 and 2, with a rod having a first diameter and using the first embodiment of the second closure element.
Figure 21:
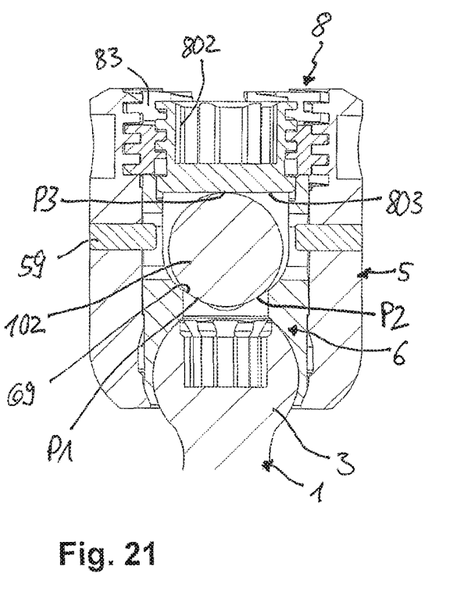
FIG. 21 shows a cross-sectional view of the anchoring assembly of FIGS. 1 and 2, with a rod having a second diameter smaller than the first diameter and using the second embodiment of the second closure element.

The second closure element 8, 8' is a two-part closure element. In a first embodiment, the second closure element 8 includes a first locking member 80 as depicted in greater detail in FIGS. 13 and 14 and a second locking member as depicted in greater detail in FIGS. 17 to 19. The first locking element 80 includes a nut which can be screwed in between the legs 55, 56 of the receiving part 5. The first locking member 80 has a first or upper end 80a and an opposite second or lower end 80b. Adjacent to its lower end 80b, a small thread-free annular surface 84 is provided at a wall of the inner bore. The nut has an external thread 81 configured to cooperate with the internal thread 57 of the legs 55, 56. Hence, the external thread 81 is preferably also a flat thread. Preferably, the inner thread 82 of the nut is also a flat thread having substantially horizontal upper and lower thread flanks. More preferably, the length of the thread flanks of the internal thread 82 in a direction perpendicular to the central axis C is smaller than the length of the thread flanks of the internal thread 57 provided at the legs 55, 56 of the receiving part. It shall be noted that the internal thread 82 can also be a metric thread or can be any other thread form. At the upper end 80a, a drive portion, such as slits 83, is provided for engagement with a driver. An axial length of the first locking member 80 may be such that when the first locking member 80 is screwed in between the legs 55, 56 of the receiving part 5 and presses onto the upper side 6a of the pressure element 6 or onto an inserted rod, the upper side 80a of the first locking member 80 may be flush with or located below the top side 5a of the receiving part in an axial direction (see FIGS. 20 and 21). The number and shape of the slits 83 may be adapted to the tool to be used.

Figure 17:
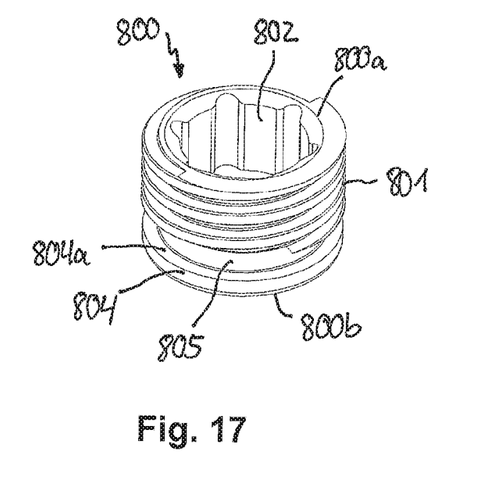
FIG. 17 shows a perspective view from a top of a second locking member of the first and second embodiments of the second closure element of the anchoring assembly shown in FIGS. 1 and 2.
Figure 18:
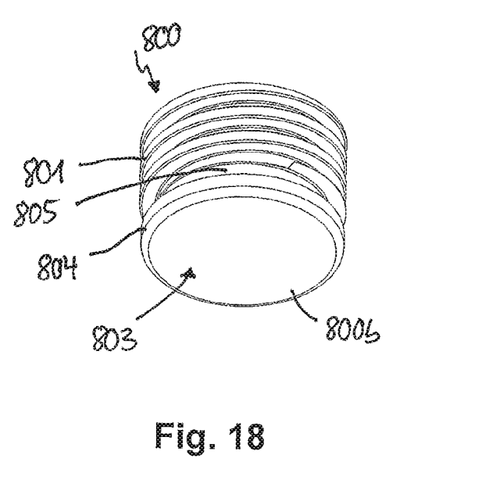
FIG. 18 shows a perspective view from a bottom of the second locking member shown in FIG. 17.
Figure 19:
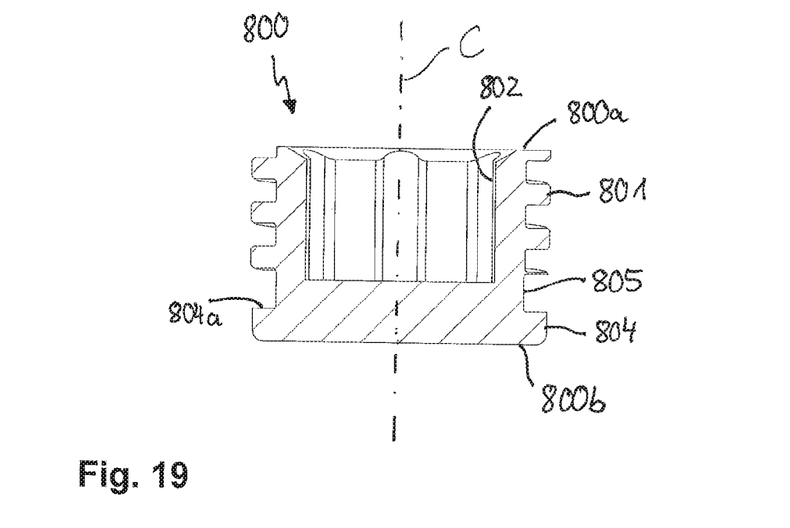
FIG. 19 shows a cross-sectional view of the second locking member of FIGS. 17 and 18, the cross-section taken in a plane including the axis of rotation of the second locking member.

Turning now to FIGS. 17 to 19, the second locking member 800 is an inner screw or set screw that is configured to be received in the first locking member 80. The second locking member 800 has an upper end 800a and an opposite lower end 800b and an external thread 801 configured to cooperate with the internal thread 82 of the nut or first locking member 80. The external thread 801 extends from the upper end 800a to a distance from the lower end 800b. At the upper end 800a, a recess 802 is provided for engagement with a driver. The recess 802 may be a hexagon-shaped recess or a torx-shaped recess, or may have any other shape suitable to cooperate with a driver. At the lower end 800b there is a substantially flat lower surface 803.

As best seen in FIG. 19, adjacent to the lower end, an annular rim 804 is formed at the outside that is followed by a thread free surface portion 805 between the annular rim 804 and the external thread 801. An upper surface 804a of the annular rim 804 that faces the external thread 801 is configured to abut against a lower thread flank 82a of the last thread turn of the internal thread 82 when the second locking member 800 is screwed into the bore of the first locking member 80 from the lower end 80b of the first locking member 80. In the assembled state of the first locking member 80 and the second locking member 800 as shown in FIG. 2, the upper surface 804a abuts against the lower thread flank 82a when the second closure element 8 is assembled for insertion into the receiving part 5. The thickness of the annular rim 804 in the axial direction is such that the lower surface 803 of the second locking member 800 is substantially flush with the lower end 80b of the first locking member 80, as shown in FIG. 2. Hence, the thread free annular surface 84 of the first locking member 80 fits around the annular rim 804 of the second locking member 800.

Figure 15:
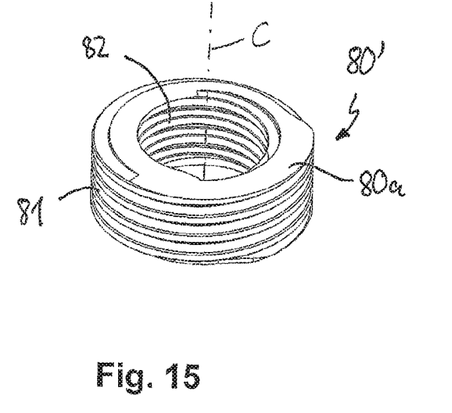
FIG. 15 shows a perspective view from a top of a second embodiment of a first locking member of a second closure element of the bone anchoring assembly shown in FIGS. 1 and 2.
Figure 16:
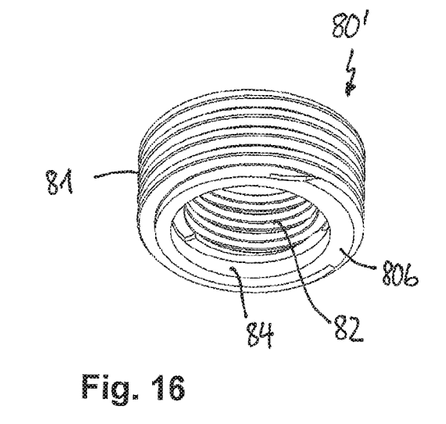
FIG. 16 shows a perspective view from a bottom of the first locking member of FIG. 15.

Next, referring to FIGS. 15 and 16 in connection with FIGS. 17 to 19, the second closure element 8' according to the second embodiment will be described. The second locking member 800 is the same for the second embodiment of the second closure element 8' as for the first embodiment. The first locking member 80' can be a nut similar to the first locking member 80 of the first embodiment of the second closure element 8. However, the nut or first locking member 80' lacks the engagement recesses 83. More generally, the first locking member 80' is free of an external drive portion that may be used to advance the first locking member 80' between the legs 55, 56 of the receiving part 5 once the second closure element 8' has been inserted into the receiving part 5.

In the assembled state, as depicted in FIG. 2, the second locking member 800 is screwed into the first locking member 80' until the upper surface 804a of the annular rim 804 abuts against a lower thread flank 82a of an internal thread 82 of the first locking member 80'. The lower surface 803 of the second locking member 800 is substantially flush with a lower end 80b of the first locking member 80'. During assembly of the first locking member 80' and the second locking member 800, the second locking member 800 is tightened with a predefined tightening torque M0 against the abutment 82a provided by the internal thread 82. By means of this, the first locking member 80' and the second locking member 800 are rotationally fixed with respect to each other in a provisional manner. To release the second locking member 800 from the provisional fixation, a torque M2 has to be applied in the opposite direction that is greater than a predetermined release torque M1. The release torque M1 may be the same or may be smaller than the tightening torque M0, because of losses due to friction and other effects. The provisional fixation prevents the second locking member 800 from being advanced towards the lower end 80b of the first locking member 80' (or more generally away from an upper end 80a of the first locking member 80') when the second locking member 800 is engaged with a tool in the engagement portion 802 and when a torque is applied that is smaller than the release torque M1. In addition, the abutment 82a prevents the second locking member 800 from passing through the upper end 80a of the first locking member 80'.

The parts and elements of the anchoring assembly may be made of preferably bio-compatible materials, for example, of titanium or stainless steel, of a bio-compatible alloy, such as NiTi-alloys, for example Nitinol, of magnesium or magnesium alloys, or from a bio-compatible plastic material, such as, for example, polyether ether ketone (PEEK) or poly-L-lactide acid (PLLA). The parts can be made of the same as or of different materials from another.

In use, the receiving part 5 may be preassembled with the pressure element 6 that is held in the receiving part, for example, via the pins 59. The receiving part 5 with pressure element 6 may then be coupled to the bone anchoring element 1. This can be done in a step prior to surgery where the head 3 is inserted through the opening 52 into the recess 63 of the pressure element 6. When the head 3 enters into the recess 63, the pressure element 6 is moved upwards in the passage 51 until further upward movement is limited by the pins 59. The flexible second portion 62 of the pressure element 6 expands in the accommodation space 53 and snaps onto the head 3. The pressure element 6 may then be pressed down so that the cooperating surfaces 53a of the receiving part and 65 of the pressure element 6 engage to preliminarily hold the head 3 in the receiving part in a pivotable manner. In another manner of use, the bone anchoring element 1 may first be inserted into the bone or a vertebra, and the receiving part 5 with preassembled pressure element 6 may then be mounted onto the head 3.

At least two bone anchoring devices are inserted into bone parts or vertebrae to be connected. One of the first rod 101 or the second rod 102 is selected and inserted into the receiving part and into channel formed by the recess 66 of the pressure element 6 of each bone anchoring device until the first rod 101 or the second rod 102 rests on the base 69. As the head 3 and consequently also the shank 2 of the bone anchoring element 1 is pivotably coupled to the receiving part 5, the receiving part 5 can be aligned to facilitate insertion of the rod. To lock the angular position of the receiving part 5 relative to the shank 2 and to fix the position of the inserted first rod 101 or second rod 102, one of the first closure element 7 or one of the two embodiments of the second closure element 8, 8' can be selected. Different closure elements may be selected for different bone anchoring devices, depending on the correction steps that have to be carried out. When the first closure element 7 is used, the inner screw forming the first closure element 7 is screwed between the legs 55, 56 until the lower surface of the projection 72 comes into contact with the upper surface of the inserted first rod 101 or second rod 102. The recesses 601 at the inner walls of the legs 67, 68 may serve as a guiding surface for the projection 72. At the time of final tightening of the inner screw, the lower surface of the projection 72 presses onto the inserted first rod 101 or second rod 102, which presses onto the base 69 of the pressure element 6. Since the first closure element 7 does not exert pressure onto the pressure element 6 but only onto the inserted first rod 101 or second rod 102, which in turn exerts pressure onto the head 3 via the pressure element 6, the head 3 and the first rod 101 or the second rod 102 are fixed simultaneously.

Loosening the first closure element 7 also releases the locking of the head 3 and the fixing of the rod simultaneously.

When the first embodiment of the second closure element 8 is used, the preassembled second closure element 8, as depicted in FIG. 2, is inserted into the receiving part 5, and the first locking member 80 is screwed down until its lower end 80b presses onto the upper end 6a of the pressure element 6. Tightening the first locking member 80 locks the angular position of the head 3 relative to the receiving part 5. Thereafter, the second locking member 800 is screwed down until its lower surface 803 contacts the first rod 101 or the second rod 102, respectively. Tightening the second locking member 800 fixes the position of the inserted rod. It shall also be noted that in some embodiments, the position of the rod can first be fixed by tightening the second locking member 800, and thereafter the angular position of the head 3 can be locked by tightening the first locking member 80.

Loosening the locking of the head 3 or the fixation of the rod can also be effected independently. This allows carrying out of various correction and/or adjustment steps in a repeated manner. A suitable tool includes independent drivers, for example, one driver for the second locking member 800 that is within a tube-shaped driver for the first locking member 80.

When using the second embodiment of the second closure element 8', a driver having only a single drive portion is sufficient. The second closure element 8' may be preassembled, wherein the second locking member 800 is tightened with the predefined tightening torque M0 against the abutment 82a of the first locking member 80'. The preassembled second closure element 8' is inserted between the legs 55, 56 of the receiving part and advanced towards the inserted first rod 101 or second rod 102, wherein the driver engages the second locking member 800 only. At the beginning, the torque applied to the second locking member 800 is smaller than the release torque M1. Therefore, the first locking member 80' and the second locking member 800 remain rotationally fixed with respect to each other in a provisional manner. When the first locking member 80' touches or engages the upper surface of the pressure element 6a with its bottom end 80b, the pressure via the pressure element 6 onto the inserted head 3 is increased as the pressure element is pressed deeper into the narrowing portion 53a. Thereby, the head 3 is clamped by friction. The strength of the clamping may depend on the dimensions of the second portion 62 of the pressure element 6 relative to the head and the force that can be exerted on the head 3 by the narrowing portion 53a of the receiving part. When an applied torque M2 applied to the second locking member 800 is greater than the release torque M1, the second locking member 800 is released from the abutment 82a and advanced through or relative to the first locking member 80'. The second locking member 800 is further advanced until the lower surface 803 contacts the inserted first rod 101 or second rod 102. The inserted first rod 101 or second rod 102 is then finally fixed by applying a torque M3 that also fully locks the entire bone anchoring device. Hence, the head and the rod are configured to be clamped and locked in a sequential manner. Releasing the locking is also sequentially effected by advancing the second locking member 800 in the opposite direction.

As shown in FIGS. 20 to 23, the inserted rod is clamped between three distinct contact areas P1, P2, P3, wherein two of the contact areas, P1, P2 are provided on the base 69 and one, P3, is provided by the lower surface 72, 803 of the selected closure element.

Assembling the first and second embodiments of the second closure element 8, 8' is easy to carry out. Since the second locking member 800 is the same for both embodiments, the number of basic components that are included in the assembly is small. Hence, the assembly or the kit, respectively, is suitable for an enlarged variety of applications.

Various further modifications of the assembly are also conceivable. While the polyaxial bone anchoring device shown is a specific type of bottom loading polyaxial bone anchoring device, a top loading polyaxial bone anchoring device may also be used. In this type, the anchoring element is inserted from the top end into the receiving part. In such an embodiment, the pressure element may be configured to press onto the upper portion of the head, which sits in a seat in the lower portion of the receiving part. Many different shapes are possible. The receiving part and/or the pressure element may also have a two part design or more. Moreover, the shape of the receiving part with pressure element is not limited to the embodiments shown. For the bone anchoring element, all types of bone anchoring elements that are suitable for anchoring in bone or vertebra may be used, in particular, also bone nails.

For the base of the pressure element and the lower surface of the first and second closure element, it is possible, to have the V-shape at the lower side of the closure element and a flat portion as a base at the pressure element. Instead of a pressure element having legs extending above the rod surface, the upper surface of the pressure element may be flat, and the second closure element may instead have downwardly extending legs that act onto the pressure element. Not only a V-shape, but any other shape that results in similar clamping of rods having different diameters may also be conceivable.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An anchoring assembly for anchoring a rod to a bone or a vertebra, the anchoring assembly comprising:
   a shank;
   a receiving part pivotably connectable to the shank, the receiving part defining a channel for receiving a rod;
   a pressure element configured to lock an angular position of the shank relative to the receiving part;
   a first rod and a second rod having different diameters and configured to be interchangeably received in the channel;
   a first closure element configured to cooperate with the receiving part, to act on the first rod when the first rod is in the receiving part for the first rod to exert pressure onto the pressure element to lock the angular position of the shank relative to the receiving part while simultaneously fixing the first rod in the channel, and to act on the second rod when the second rod is in the receiving part for the second rod to exert pressure onto the pressure element to lock the angular position of the shank relative to the receiving part while simultaneously fixing the second rod in the channel; and
   a second closure element configured to cooperate with the receiving part, wherein the second closure element is configured to act on the pressure element to lock the angular position of the shank relative to the receiving part and to act separately on the first rod or the second rod to fix the first rod or the second rod in the channel;
   wherein the first closure element and the second closure element are configured to interchangeably cooperate with the receiving part.

2. The anchoring assembly of claim 1, wherein the pressure element defines a recess that forms a base and two free legs configured to extend above first rod or the second rod when either the first rod or the second rod is respectively inserted into the recess and rests on the base.

3. The anchoring assembly of claim 1, wherein when either the first rod or the second rod is received in the channel between the pressure element and the first closure element, the pressure element and the first closure element are configured to clamp the first rod or the second rod at at least three distinct contact areas, and wherein when either the first rod or the second rod is received in the channel between the pressure element and the second closure element, the pressure element and the second closure element are configured to clamp the first rod or the second rod at at least at three distinct contact areas.

4. The anchoring assembly of claim 3, wherein the pressure element has a base on which two of the distinct contact areas are located.

5. The anchoring assembly of claim 3, wherein the distinct contact areas each forms a line substantially parallel to a longitudinal axis of the channel.

6. The anchoring assembly of claim 3, wherein one of the distinct contact areas is located on a lower side of the first closure element or on a lower side of the second closure element.

7. The anchoring assembly of claim 1, wherein the first closure element and the second closure element each comprises a projection that has a length such that when either the first closure element or the second closure element is inserted into the receiving part and advanced therein, the inserted closure element is configured to contact the first rod when the first rod is in the channel, and to contact the second rod when the second rod is in the channel.

8. The anchoring assembly of claim 1, wherein the first closure element is a single monolithic part, and wherein when the first rod or the second rod is in the channel and the first closure element is inserted into the receiving part, the first closure element is configured to directly exert pressure onto the first rod or the second rod while a gap remains in an axial direction between the pressure element and a lower side of the first closure element.

9. The anchoring assembly of claim 1, wherein the second closure element comprises a first locking member and a second locking member positionable in the first locking member, wherein the first locking member is configured to directly exert pressure on the pressure element and the second locking member is configured to directly exert pressure on the first rod or the second rod.

10. The anchoring assembly of claim 9, wherein a stop is provided on the first locking member to limit an advancement of the second locking member relative to the first locking member, wherein the stop is at or close to a lower end of the first locking member and faces the pressure element when the pressure element and the second closure element are in the receiving part.

11. The anchoring assembly of claim 10, wherein the stop is formed by a thread flank of an internal thread of the first locking member.

12. The anchoring assembly of claim 11, wherein a lower end of the second locking member comprises a ring-shaped projection configured to abut against the stop formed by the thread flank of the internal thread of the first locking member.

13. The anchoring assembly of claim 9, wherein the first locking member and the second locking member are independently drivable from one another relative to the receiving part.

14. The anchoring assembly of claim 9, wherein in a first configuration, the first locking member and the second locking member are rotationally fixed relative to one another and movable together relative to the receiving part.

15. The anchoring assembly of claim 14, wherein in a second configuration, the second locking member is rotatable relative to both the first locking member and the receiving part, and wherein the first and second locking members are adjustable from the first configuration to the second configuration by applying a torque to the second locking member that is greater than a holding force between the first and second locking members to release the rotational fixation between the first and second locking members.

16. The anchoring assembly of claim 9, wherein the second closure element comprises a single drive portion at the second locking member, without a separate drive portion provided at the first locking member.

17. The anchoring assembly of claim 9, further comprising a third locking member that is different structurally from the first locking member and that is configured to directly exert pressure on the pressure element, wherein the second closure element can be formed either by connecting the second locking member to the first locking member or by connecting the second locking member to the third locking member.

18. The anchoring assembly of claim 1, wherein the diameter of the first rod is greater than the diameter of the second rod, wherein the pressure element defines a recess that forms a base and two free legs configured to extend above the second rod when the second rod rests on the base, and wherein the first closure element comprises a projection with a length that is greater than a minimum axial distance between free ends of the two free legs and the second rod when the second rod rests on the base.

19. A closure element for a polyaxial bone anchoring device, the closure element comprising:
    a first locking member comprising a first end, a second end, and an inner surface defining a bore that extends from the first end to the second end, wherein an internal thread is formed on the inner surface with a lower thread flank that is positioned closest to the second end but distinct from an end face at the second end; and
    a second locking member that is insertable from the second end of the first locking member into the bore of the first locking member, the second locking member having a first end that is directed towards the first end of the first locking member during insertion, a second end, an external thread configured to engage the internal thread of the first locking member, and an abutment surface near the second end of the second locking member, wherein the abutment surface faces the first end of the second locking member and is distinct from the external thread;
  wherein the lower thread flank of the internal thread of the first locking member forms a stop, and wherein the abutment surface of the second locking member is configured to abut against the stop to limit advancement of the second locking member towards the first end of the first locking member when the second locking member is inserted in the first locking member.

20. The closure element of claim 19, wherein the second locking member is configured to be rotationally fixed relative to the first locking member via a holding force, and wherein when a torque greater than the holding force is applied to the second locking member, the rotational fixation between the first and second locking members is released and the second locking member becomes rotatable relative to the first locking member.

21. The closure element of claim 19, wherein the second locking member is monolithic.

22. The closure element of claim 19, wherein the stop formed by the lower thread flank of the internal thread is recessed from the end face at the second end of the first locking member.

23. A method of anchoring a rod to a bone or a vertebra via an anchoring assembly comprising a shank, a receiving part pivotably connectable to the shank, the receiving part defining a channel for receiving a rod, a pressure element configured to lock an angular position of the shank relative to the receiving part, a first rod and a second rod having different diameters and configured to be interchangeably received in the channel, and a first closure element and a second closure element configured to interchangeably cooperate with the receiving part, the method comprising:
    anchoring the shank of the anchoring assembly to the bone or the vertebra;
    adjusting an angular position of the receiving part relative to the shank;

selecting and inserting one of the first rod or the second rod into the channel of the receiving part;

selecting and inserting one of the first closure element or the second closure element into the receiving part, wherein when the first closure element is inserted into the receiving part, the first closure element is configured to act on the first rod when the first rod is in the receiving part for the first rod to exert pressure onto the pressure element to lock the angular position of the shank relative to the receiving part while simultaneously fixing the rod in the channel, and to act on the second rod when the second rod is in the receiving part for the second rod to exert pressure onto the pressure element to lock the angular position of the shank relative to the receiving part while simultaneously fixing the second rod in the channel, and wherein when the second closure element is inserted into the receiving part, the second closure element is configured to act on the pressure element to lock the angular position of the shank relative to the receiving part and to act separately on the selected rod to fix the rod in the channel.

* * * * *